United States Patent
Pfeuffer (10) Patent No.: US 9,341,694 B2
(45) Date of Patent: May 17, 2016

(54) METHOD AND MAGNETIC RESONANCE SYSTEM FOR DISTORTION CORRECTION IN MAGNETIC RESONANCE IMAGING

(75) Inventor: Josef Pfeuffer, Kunreuth (DE)

(73) Assignee: Siemens Aktiengesellschaft, Munich (DE)

( * ) Notice: Subject to any disclaimer, the term of this patent is extended or adjusted under 35 U.S.C. 154(b) by 783 days.

(21) Appl. No.: 13/491,854

(22) Filed: Jun. 8, 2012

(65) Prior Publication Data

US 2012/0313640 A1    Dec. 13, 2012

(30) Foreign Application Priority Data

Jun. 8, 2011   (DE) .................. 10 2011 077 197

(51) Int. Cl.
| | |
|---|---|
| G06K 9/40 | (2006.01) |
| G01R 33/34 | (2006.01) |
| G01R 33/565 | (2006.01) |
| A61B 5/055 | (2006.01) |
| G01R 33/48 | (2006.01) |
| G01R 33/561 | (2006.01) |

(52) U.S. Cl.
CPC .......... *G01R 33/56572* (2013.01); *A61B 5/055* (2013.01); *G01R 33/4824* (2013.01); *G01R 33/5616* (2013.01); *G01R 33/56554* (2013.01)

(58) Field of Classification Search
CPC ..................... G01R 33/56572; G01R 33/5616; G01R 33/56554; G01R 33/56509; G01R 33/5676; G01R 33/56536; G01R 33/4824; G01R 33/56563; A61B 5/055
USPC ............................ 324/307, 309, 318; 382/131
See application file for complete search history.

(56) References Cited

U.S. PATENT DOCUMENTS

| | | | | |
|---|---|---|---|---|
| 5,910,728 | A * | 6/1999 | Sodickson | G01R 33/3815 324/309 |
| 6,020,739 | A * | 2/2000 | Meyer et al. | 324/309 |
| 6,067,465 | A | 5/2000 | Foo et al. | |
| 6,850,061 | B2 * | 2/2005 | Stoyle | 324/306 |
| 7,205,763 | B2 * | 4/2007 | Porter | 324/306 |
| 7,711,166 | B2 * | 5/2010 | Mistretta et al. | 382/128 |
| 2009/0195247 | A1 | 8/2009 | Pfeuffer et al. | |

(Continued)

OTHER PUBLICATIONS

Ahn et al., High-Speed Spiral-Scan Echo Planar NMR Imaging-I, Mar. 1986, IEEE Transactions on Medical Imaging, vol. MI-5, No. 1, pp. 2-7.*
Magnetic Resonance Angiography, Arlart et al. (2002), pp. 70-73.

(Continued)

*Primary Examiner* — Melissa Koval
*Assistant Examiner* — Rishi Patel
(74) *Attorney, Agent, or Firm* — Schiff Hardin LLP (57) ABSTRACT

In a method for distortion correction in spiral magnetic resonance imaging, a first MR data set is acquired by scanning raw data space along a spiral trajectory beginning at a first point. A first complex MR image is determined from the first MR data set, which includes first phase information for image points of the first MR image. A second MR data set is acquired by scanning raw data space along the spiral trajectory beginning at a second point that differs from the first point. A second complex MR image is determined from the second MR data set, which includes second phase information for image points of the second MR image. A geometric distortion for image points of the first or second MR image is determined from the first and second phase information, for example with a PLACE method.

27 Claims, 6 Drawing Sheets

(56) References Cited

U.S. PATENT DOCUMENTS

2011/0260726 A1 10/2011 Techavipoo et al.
2012/0013336 A1* 1/2012 Hetzer ............... G01R 33/4818
324/309

OTHER PUBLICATIONS

"Reducing Distortions in Diffusion-Weighted Echo Planar Imaging With a Dual-Echo Blip-Reversed Sequence," Gallichan et al., Magnetic Resonance in Medicine, vol. 64 (2010), pp. 382-390.

"Spiral-In/Out Bold fMRI for Increased SNR and Reduced Susceptibility Artifacts," Glover et al., Magnetic Resonance in Medicine, vol. 46 (2001), pp. 515-522.

"Real-time MRI at a resolution of 20 ms," Uecker et al., NMR in Biomedicine, vol. 23 (2010), pp. 986-994.

"Correction for Geometric Distortion and N/2 Ghosting in EPI by Phase Labeling for Additional Coordinate Encoding (PLACE)," Xiang et al., Magnetic Resonance in Medicine, vol. 57 (2007), pp. 731-741.

* cited by examiner

METHOD AND MAGNETIC RESONANCE SYSTEM FOR DISTORTION CORRECTION IN MAGNETIC RESONANCE IMAGING

BACKGROUND OF THE INVENTION

1. Field of the Invention

The present invention concerns methods for magnetic resonance imaging that can be used in medical engineering to examine patients. The present invention in particular concerns methods to correct distortions or deformations in the phase coding direction that can occur given a use of echoplanar sequences (known as EPI sequences) and that can negatively affect image quality.

The present invention likewise concerns a magnetic resonance system for implementing such methods.

2. Description of the Prior Art

Magnetic resonance tomography (MRT), which is used for magnetic resonance imaging, is based on the physical principle of nuclear magnetic resonance. In magnetic resonance tomography, an examination subject (a patient, for example) is exposed to a constant, strong magnetic field. The nuclear spins of the atoms in the subject, which were previously oriented at random, thereby align. Radio-frequency waves can excite these aligned nuclear spins into a precession movement that causes the actual measurement signal in the magnetic resonance tomography apparatus. The measurement signal can be acquired with suitable reception coils. The examination subject can be spatially coded in all three spatial directions by the use of non-homogeneous magnetic fields that can be generated by gradient coils.

In one possible method to generate magnetic resonance images (MR images), a slice is initially selectively excited in the z-direction, for example. The coding of the spatial information in the slice takes place via a combined phase and frequency coding by means of two orthogonal gradient fields that (in the example of a slice excited in the z-direction) are generated by gradient coils in the x-direction and y-direction. The imaging sequence is repeated for varying values of the phase coding gradient, wherein the nuclear magnetic resonance signal is acquired multiple times in each sequence pass in the presence of the readout gradient. A number matrix in a mathematical domain known as raw data space or k-space is obtained in this way. A magnetic resonance image of the excited slice can be reconstructed from this number matrix through a Fourier transformation.

An additional method to generate magnetic resonance images is known as echoplanar imaging (EPI). Multiple phase-coded echoes are used to fill the raw data matrix. After a single (selective) radio-frequency excitation, a series of echoes is generated in the readout gradient that are associated in raw data space with different lines in the excited slice by a suitable modulation of the phase coding gradient.

Figure 1:
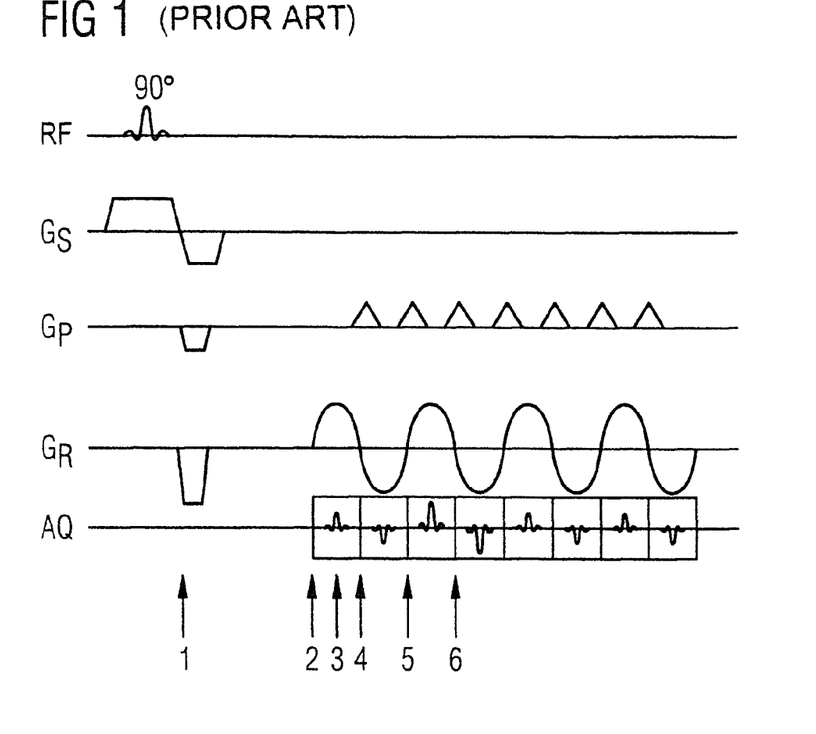
FIG. 1 shows a sequence diagram of an echoplanar imaging sequence according to the prior art.
Figure 2:
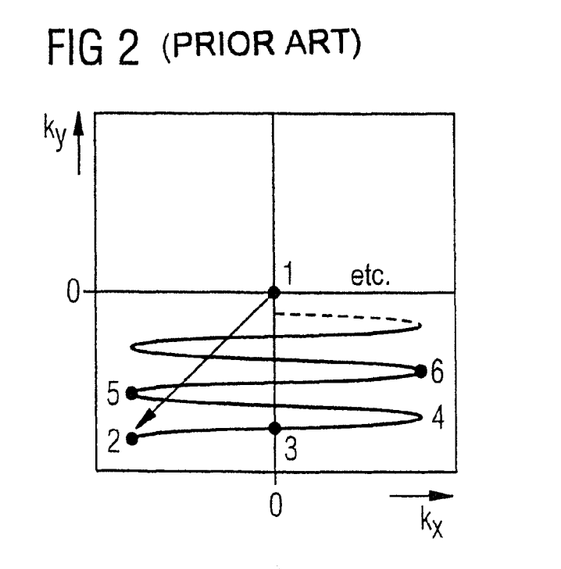
FIG. 2 schematically shows a meandering (serpentine) scan of the raw data space in an echoplanar imaging sequence.

An example of an echoplanar pulse sequence is shown in FIG. 1. After an excitation pulse and a refocusing pulse, multiple gradient echoes are generated by a sinusoidally oscillating frequency coding gradient $G_R$ in the readout direction and phase coding. In this representation the phase coding takes place by small gradient pulses (known as blips) of the phase coding gradient $G_p$ in the region of the zero crossings of the oscillating frequency coding gradient $G_R$, and this leads to a wandering traversal of the raw data space (as shown in FIG. 2). EPI alternatively can be implemented as a Cartesian EPI with a rectangular curve of the readout gradient $G_R$, for example, or as a non-Cartesian EPI (for example spiral EPI or radial EPI).

EPI sequences have extremely short measurement times, typically of 30-50 ms for one MR image acquisition per 2D slice. Such sequences are particularly suitable in functional imaging and in perfusion and diffusion measurements since movement artifacts (due to breathing or pulsing motion of blood or fluid, for example) can be drastically reduced. A problem with such fast imaging methods, however, is their high sensitivity to $B_0$ field distortions or induced susceptibilities, since the readout time per excitation is significantly longer compared to other methods that acquire only portions of a line or one line in raw data space.

Figure 3:
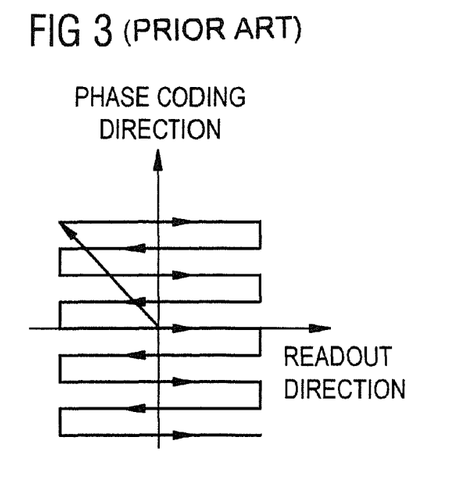
FIGS. 3 and 4 show the trajectories in the raw data space of two successive echoplanar imaging measurements with a phase offset of one line in the phase coding direction, for a PLACE method.
Figure 4:
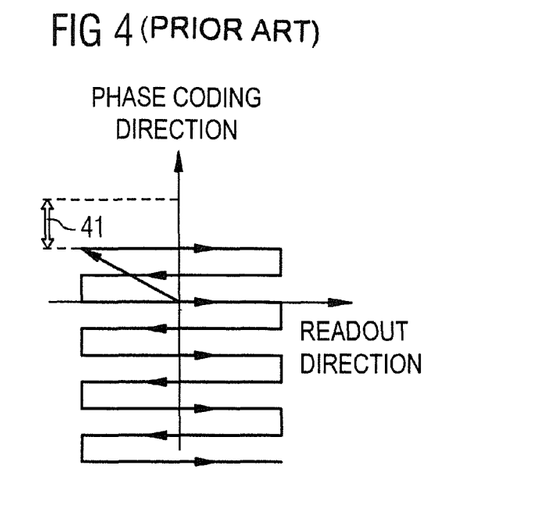

Methods are known with which information about the inhomogeneities of the magnetic field can be derived from two k-space trajectories that are adjacent to one another, but displaced in the phase coding direction. A field map or a displacement map can be determined from this information. Such a field map shows magnetic field distortions or magnetic field shifts, while a displacement map includes the original positions (or the offset relative to the original position) of the image points of the magnetic resonance images that were distorted or displaced in the phase coding direction due to these magnetic field shifts or magnetic field inhomogeneities. Such a method to create displacement maps is what is known as the PLACE method (Phase Labeling for Additional Coordinate Encoding). This PLACE method is described in detail in the publication by Qing-San Xiang and Frank Q. Ye with the title "Correction for Geometric Distortion and N/2 Ghosting in EPI by Phase Labeling for Additional Coordinate Encoding (PLACE)", Magnetic Resonance in Medicine 57:731-741 (2007), and is therefore only briefly outlined in the following using FIGS. 3 and 4. In the PLACE method, two echoplanar imagings with Cartesian scanning [sampling] are implemented in succession. The first scan (shown in FIG. 3) is implemented in a typical manner in that a k-space trajectory is traversed in a wandering pattern. For clarity, the number of lines in the phase coding direction amounts to only nine in FIG. 3 and is significantly higher (for example 32-256) in real echoplanar imagings. After this, a second echoplanar imaging is implemented which is shifted by one or more lines in the phase coding direction, for example. FIG. 4 shows such a k-space trajectory which was shifted by two lines, as represented by the double arrow 41. Physically, the gradient range that is thus added generates a relative phase ramp across the examination subject and directly codes the undeformed original coordinates in the phase coding direction of each image point in a phase difference between the two distorted complex images which were acquired from the first imaging according to FIG. 3 and the second imaging according to FIG. 4. The phase information is then used in order to map the distorted signals to their original locations. Expressed in a different way, the image point distortion (image point deformation or image point shift) can be determined from the phase information of the offset k-space trajectories of two pre-interventional EPI images. From this a displacement map can be determined which can be applied to the acquired images.

Typically, 200-300 images are acquired per volume in a functional EPI measurement (typically 40-60 slices per volume). DE 10 2008 007 048 B4 describes a method for dynamic distortion correction in EPI measurements in which immediately successive image acquisitions differ in an alternating or otherwise periodic manner with regard to phase information, phase coding direction or with regard to the echo time, and due to this difference a field map and/or a displacement map with which at least one distorted result image is corrected is respectively calculated from pairs of immediately successive image acquisitions. According to one embodiment, corresponding field maps or displacement maps are determined with the use of the previously described PLACE method from pairs of immediately successive image acquisitions.

As previously described, the two EPI measurements that are used in the PLACE method differ in that k-space is scanned in two trajectories that are shifted in the phase coding direction, and therefore cannot be applied for non-Cartesian scans (for example spiral-shaped or radial scans as are known from Gary H. Glover and Christine S. Law in "Spiral-In/Out BOLD fMRI for Increased SNR and Reduced Susceptibility Artifacts" in Magnetic Resonance in Medicine, 46:515-522 (2001), for example). Furthermore, in the PLACE method corresponding lines in k-space of the two EPI measurements are acquired at different echo times. Different amplitudes (and thus different magnitude images) thereby result. The magnitude images therefore are not directly comparable with one another.

SUMMARY OF THE INVENTION

An object of the present invention is to improve a distortion correction in magnetic resonance imaging, particularly in the case of a spiral-shaped or radial scanning.

According to the present invention, a method is provided for distortion correction in a spiral magnetic resonance imaging procedure. In spiral magnetic resonance imaging, in order to acquire a magnetic resonance data set (MR data set), raw data space (known as k-space) is scanned with a spiral trajectory after a single radio-frequency excitation by means of a modulation of at least two readout gradients in at least two spatial directions. The spiral magnetic resonance imaging can include, for example, spiral echoplanar imaging in which the raw data space is scanned with a spiral trajectory with two readout gradients in two spatial directions (X and Y, for example). In the single radio-frequency excitation, a slice in raw data space can be excited, for example, so that a plane in raw data space is scanned in a spiral shape with the aid of the X and Y readout gradients. Furthermore, the spiral magnetic resonance imaging can include a 3D imaging in which the raw data space is scanned with a spiral trajectory by means of a modulation of three readout gradients in three spatial directions. In the inventive method, a first MR data set is acquired in the raw data space in that said raw data space is scanned along a spiral-shaped trajectory, beginning at a first point of the raw data space. A first complex magnetic resonance image (MR image) is determined depending on the first MR data set. The first complex MR image comprises a phase information for image points of the first MR pixel. The first complex MR image furthermore can include an amplitude information for image points of the first MR image. According to the method, a second MR data set is acquired in the raw data space. For this purpose, the raw data space is scanned along the spiral-shaped trajectory beginning at a second point of said raw data space. The second point is different than the first point, meaning that the spiral-shaped trajectory is scanned beginning from a different start point in the acquisition of the second MR data set than in the acquisition of the first MR data set. A second complex MR image is determined depending on the second MR data set. The second complex MR image includes a second phase information for image points of the second MR image. The second MR image can additionally include an amplitude information for image points of the second MR image. Depending on the first and second phase information, a geometric distortion is determined for image points of the first or second MR image. With the method described in the preceding, two complex magnetic resonance images thus can be determined that contain phase information that can be used (as in the previously described PLACE method) in order to determine geometric distortions from these and to correct the MR images accordingly. For example, a field and/or displacement map with which the arrangement of image points of the first or second MR image can be corrected can be determined on the basis of the PLACE method.

Depending on the application, the spiral-shaped trajectory can begin with a predetermined radius which decreases along the trajectory or which increases along the trajectory. Expressed differently, the spiral-shaped trajectory can either run from the outside in or from the inside out.

Furthermore, according to the present invention a method is provided for distortion correction in a radial magnetic resonance imaging procedure. In radial magnetic resonance imaging, raw data space is essentially scanned with a radial trajectory to acquire a magnetic resonance data set after a single radio-frequency excitation by means of a modulation of two readout gradients in two spatial directions (X, Y for example) or by means of a modulation of three readout gradients in three spatial directions (X, Y, Z). In the method, a first MR data set is acquired in the raw data space by the raw data space being scanned along a trajectory through the center of the raw data space, beginning at a first point of said raw data space, and in total multiple trajectories are acquired with different angles through the center of the raw data space. The multiple trajectories can also include trajectories that essentially run through the center of the raw data space, for example as in a radial magnetic resonance imaging. Depending on the first MR data set, a first complex MR image is determined which comprises a first phase information for image points of the first MR image. In the raw data space a second MR data set is acquired in that the raw data set is scanned along the same trajectory, beginning at a second point of the raw data space. The second point, i.e. the start point of the second MR data set, is different from the first. Depending on the second MR data set, a second complex MR image is determined which comprises a second phase information for image points of the second MR image. A geometric distortion for image points of the first or second MR image is determined from the first and second phase information. The geometric distortion correction can include a determination of a field or displacement map on the basis of the PLACE method, for example.

Even in non-Cartesian echoplanar imaging (such as spiral echoplanar imaging or radial MR imaging, for example), it is possible to determine and correct a geometric distortion of the image points, similar to as in Cartesian echoplanar imaging.

According to one embodiment, the raw data space is scanned with a varying speed along the trajectory. Furthermore, the raw data space can be scanned with a varying density along the trajectory. The scanning of the raw data space can thereby be adapted to requirements of the resulting magnetic resonance images (for example resolution or contrast) or to a desired acquisition speed.

According to the present invention, an additional method is provided for distortion correction in an echoplanar imaging procedure for magnetic resonance imaging. In echoplanar imaging, raw data space is scanned to acquire an MR data set after a single radio-frequency excitation by means of a modulation of a readout gradient and a phase coding gradient. In the method, a first MR data set is acquired in the raw data space according to the echoplanar imaging, wherein the raw data space is scanned along a predefined trajectory, beginning at a first point of the raw data space. For example, the trajectory can be Cartesian or (as in the methods described in the preceding) also non-Cartesian. A first complex MR image is determined depending on the first MR data set. The first complex MR image comprises a phase information for image points of the first MR image. Furthermore, a second MR data set in the raw data space is acquired in that the raw data space is scanned along the predefined trajectory, beginning at a second point of said raw data space. The second point is different than the first point, meaning that although the first and second points lie on the same trajectory, they are at different positions. A beginning of the modulation of the readout gradient and the phase coding gradient is additionally delayed in the acquisition of the second MR data set after the single radio-frequency excitation, such that points of the trajectory are scanned at the same points in time (relative to the radio-frequency excitation) in the acquisition of the second MR data set as the corresponding points of the trajectory in the acquisition of the first MR data set.

Expressed differently, two MR data sets are acquired according to an echoplanar imaging. MR data values of the raw data set are scanned and acquired in series along the predefined trajectory. The acquisition of the first MR data set begins at a first point of the raw data set, for example. In contrast, the acquisition of the second MR data set begins at a second point on the same trajectory but is only acquired later in the acquisition of the first MR data set (thus after the acquisition of the first point). The distance between the first point and the second point can amount to multiple sample points, for example, or—in the case of a Cartesian EPI—the distance between the first point and the second point can comprise one or more lines of the Cartesian scan. The echoplanar imaging to acquire the first MR data set has a single radio-frequency excitation, and the echoplanar imaging to acquire the second MR data set likewise has a single radio-frequency excitation. The scanning of the raw data space to acquire the second MR data set is chronologically placed relative to the radio-frequency excitation so that points of the predefined trajectory that are scanned in both echoplanar imagings are scanned at an identical point in time relative to the respective radio-frequency excitations. This can be achieved by inserting an appropriate delay time period between the beginning of the modulation of the readout gradient and the phase coding gradient in the acquisition of the second MR data set.

Depending on the first MR data set, a first complex MR image is determined which comprises a first phase information for image points of the first MR image. Depending on the second MR data set, a second complex MR image is determined which comprises a second phase information for image points of the second MR image. Depending on the first and second phase information, a geometric distortion of image points of the first and/or second MR image is determined. The geometric distortion can be determined in the form of a field map or displacement map on the basis of the PLACE method, for example. Corresponding points of the trajectory in the acquisition of the first MR data set and in the acquisition of the second MR data set are acquired at the same echo times due to the insertion of the delay between the radio-frequency excitation of the second echoplanar imaging and the acquisition of the second MR data set. Absolute values of corresponding image points in the first complex MR image and the second complex MR image are comparable with one another so that these absolute values can reasonably be correlated in the evaluation of the MR images.

In a further method according to the present invention, distortion correction is provided in magnetic resonance echoplanar imaging. In the method an examination subject is excited with a single radio-frequency excitation for an acquisition of at least one first MR data set and one second MR data set. Expressed differently, only one radio-frequency excitation is applied for slice selection, for example, and the first and second MR data set are thereupon acquired as described in the following. No additional radio-frequency excitation is implemented between the acquisition of the first MR data set and the acquisition of the second MR data set. The first MR data set is acquired in a raw data space in that the raw data space is scanned—beginning with a first point of said raw data space—along a predefined trajectory by means of a modulation of a readout gradient and a phase coding gradient. Furthermore, the second MR data set is acquired in a raw data space in that the raw data space is scanned—beginning with a second point of said raw data space—along a predefined trajectory. The second point is different than the first point. A first complex MR image that includes first phase information for image points of the first MR image is determined depending on the first MR data set. A second complex MR image is determined depending on the second MR data set. The second complex MR image includes second phase information for image points of the second MR image. Depending on the first and second phase information, a geometric deformation for image points of the first or second MR image is determined (for example in the form of a field map or displacement map) on the basis of the PLACE method. The first MR data set and the second MR data set are thus acquired with the use of a multi-echo sequence within an MR excitation, instead of with two individual echo sequences with two different MR excitations as are used in the PLACE method. The first MR data set and the second MR data set can be acquired at an interval of a few milliseconds (for example at an interval of 50 to 100 ms) so that only slight differences can occur in the first and second MR data set due to movements of the examination subject or temporal B0 field changes, so a reliable correction of the distortion is possible with the use of the phase information.

According to one embodiment, the previously described echoplanar imaging with a single radio-frequency excitation for the first MR data set and the second MR data set can comprise a multi-spin echo sequence in which a first radio-frequency refocusing pulse is applied before the acquisition of the first MR data set and a second radio-frequency refocusing pulse is applied between the acquisition of the first MR data set and the acquisition of the second MR data set. The first refocusing pulse can also include a magnetic preparation, for example an adjustment of diffusion weighting gradients. The diffusion weighting gradient can be adjusted in an arbitrary direction, for example in a readout direction or in a phase coding direction. The individual excitation for the acquisition of the first and second MR data set is particularly advantageous when the time period for the difference preparation primarily influences the duration of the acquisition sequence. With the (thus shortened) echoplanar imaging, the use of multiple refocused echoes within the T2 relaxation time is possible. To further accelerate the echoplanar imaging method, the method can be combined with methods for parallel imaging (Parallel Acquisition Technique PAT or Parallel Imaging PI) or what is known as "Zoomed Echoplanar Imaging" with reduced field of view, or a segmented echoplanar imaging with a segmented readout or phase direction.

Although the previously described methods for distortion correction have been described separately, the previously described methods and their embodiments can be combined with one another arbitrarily.

Furthermore, according to the present invention a magnetic resonance system is provided which comprises a basic field magnet, a gradient field system, a radio-frequency antenna and a control device. The control device controls the gradient field system and the radio-frequency antenna. Furthermore, the control device receives measurement signals that are acquired by the radio-frequency antenna and evaluates the measurement signals in order to create magnetic resonance images. Furthermore, the control device is designed to implement one or more of the previously described methods. For example, the control device is designed to acquire an MR data set in a raw data space according to a spiral magnetic resonance imaging. In the spiral magnetic resonance imaging, the raw data space is scanned in a spiral shape (in that readout gradients are modulated) to acquire the MR data set after a single radio-frequency excitation. The raw data space is scanned along a spiral-shaped trajectory, beginning at a first point of the raw data space. Furthermore, the control device is designed to determine a first complex MR image depending on the first MR data set. The first complex MR image includes first phase information for image points of the first complex MR image. Furthermore, the control device is designed in order to acquire a second MR data set in the raw data space according to the spiral echoplanar imaging. The raw data space is scanned along the spiral-shaped trajectory beginning at a second point of the raw data space. The second point is different than the first point. For example, the second point can be a point on the spiral-shaped trajectory that is scanned chronologically after the scanning of the first point in the acquisition of the first MR data set. Depending on the second MR data set, the control device determines a second complex MR image that includes second phase information for image points of the second MR image. Furthermore, the control device determines a geometric distortion for image points of the first or second MR image depending on the first and second phase information. The geometric distortion can be determined in the form of a field map or displacement map (for example) on the basis of the PLACE method.

Since the magnetic resonance system can be designed to implement one or more of the previously described methods, it also includes the previously described advantages.

The above object also is achieved in accordance with the present invention by a non-transitory, computer-readable data storage medium encoded with programming instructions (commands) that, when executed, cause a computer in which the storage medium is loaded to control and/or operate a magnetic resonance imaging system to implement one or more of the embodiments of the methods described above.

The computer program product may require program means (libraries or auxiliary functions, for example) in order to realize the corresponding embodiments of the method. The software can be source code (C++, for example) that must still be compiled or translated and linked or which must only be interpreted, or executable software code that has only to be loaded into the corresponding processing unit for execution.

The electronically readable data medium can be a CD, a DVD, a magnetic tape or a USB stick) on which is stored electronically readable control information (in particular software as has been previously described). All embodiments according to the invention of the described method can be implemented when this control information or software is read from the data medium and stored in the processing unit.

DESCRIPTION OF THE PREFERRED EMBODIMENTS

Figure 5:
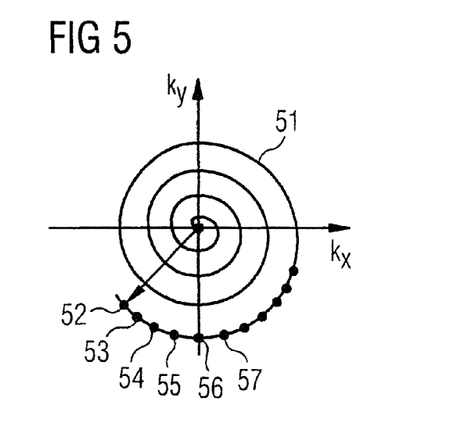
FIG. 5 and FIG. 6 show a spiral-shaped raw data space scan of a magnetic resonance imaging measurement according to one embodiment of the present invention.

FIG. 5 shows a trajectory 51 in an X/Y plane of the raw data space (what is known as k-space). The trajectory 51 travels in the shape of as spiral from the outside in and ends at the middle point of the raw data space. Data are acquired along the trajectory 51 to fill the raw data space at points 52-57. Additional sample points are present on the trajectory but are not provided with additional reference characters for clarity. Moreover, additional sample points are present along the trajectory 51 but are likewise not drawn in FIG. 5 for clarity. The additional sample points proceed along the trajectory 51 up to the middle point of the spiral-shaped trajectory 51.

Figure 7:
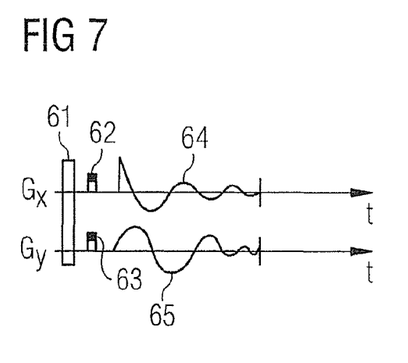
FIG. 7 shows a sequence diagram for a magnetic resonance imaging sequence for a scan of the raw data space according to FIG. 5 or FIG. 6.

FIG. 7 shows a sequence diagram of the gradients $G_x$ and $G_y$ in order to scan the raw data space in a spiral shape as shown in FIG. 5. For this purpose, a single slice of the raw data space is initially selected and excited with a radio-frequency pulse. This excitation is not shown in detail in FIG. 7, but rather is represented in a generalized form by Block 61. By applying the gradients 62 and 63, the start point (prephaser)—the point 52 in FIG. 5, for example—of the trajectory 51 is set. Additional points 52-57 as well as additional points along the trajectory 51 are read out by applying suitable X and Y readout gradients 64, 65. The gradients 64 and 65 shown in FIG. 7 are only schematically depicted. Details regarding spiral echoplanar imaging are described in the publication by Gary H. Glover and Christine S. Law "Spiral In/Out BOLD fMRI for Increased SNR and reduced Susceptibility Artifacts".

Figure 6:
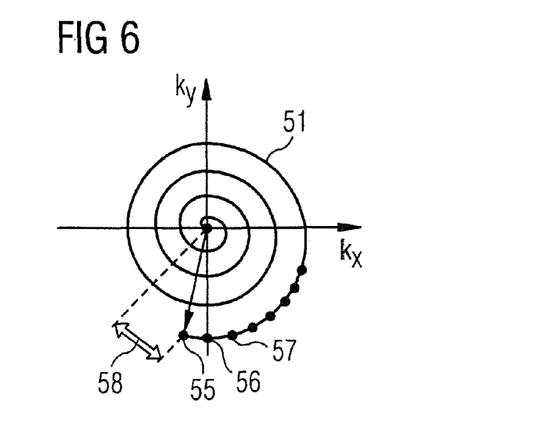

In order to correct distortions (which can be caused by B0 field changes or induced susceptibilities due to the long readout time per excitation), two spiral echoplanar measurements are implemented. In the first measurement, the scan as shown in FIG. 5) begins at point 52, followed by point 53, point 54, point 55, point 56, point 57 etc. K-space is filled on the basis of this EPI measurement and a first complex MR image is created with the aid of a Fourier transformation. For each image point the MR image includes magnitude information and phase information. Following this, a second EPI measurement is implemented in which the scan in the raw data space begins at point 55, as shown in FIG. 6. The points 56, 57 etc. along the trajectory 51 are subsequently scanned. K-space is filled with the sample values and a second complex magnetic resonance image is created with the aid of a Fourier transformation. In the second complex magnetic resonance image, phase information and a magnitude information are likewise associated with each image point. According to the PLACE method, a distortion can now be determined for each image point from the phase difference of the image points of the first and second complex magnetic resonance image, and the positions of the image points can thus be corrected. The physical basis for this is that a relative phase ram across the subject was generate by an offset 58 between the start points 52 (FIG. 5) and 55 (FIG. 6) of the two EPI measurements, and the undistorted original coordinates of each image point are directly coded in a phase difference between the two distorted complex images.

Figure 8:
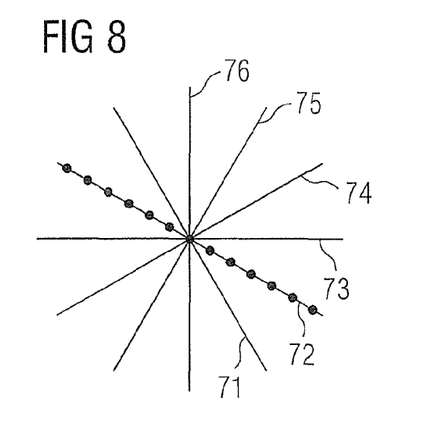
FIG. 8 shows a radial raw data space scan of a magnetic resonance imaging measurement according to one embodiment of the present invention.
Figure 9:
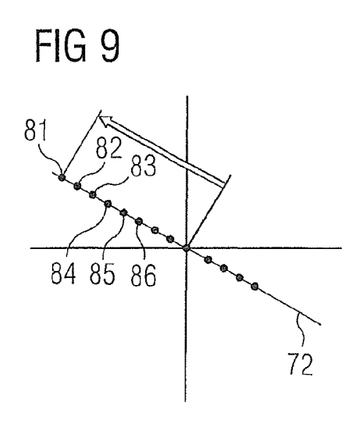
FIG. 9 and FIG. 10 show details of the radial raw data space scan according to FIG. 8.
Figure 10:
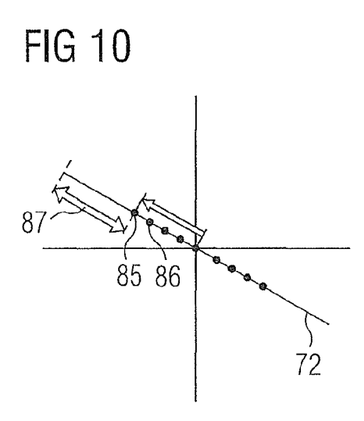

FIG. 8 shows a trajectory for scanning of the raw data space in a radial MR imaging. The trajectory includes straight lines 71-76 that travel through the center of the raw data space and are scanned in sequence along the respective straight lines. Sample points are shown as examples on the straight line 72 in FIG. 8. FIG. 9 shows the straight line 72 in detail. For example, the straight line 72 can be scanned beginning with the point 81, followed by the point 82, the point 83 etc. Corresponding sequence diagrams for scanning k-space in the radial direction are known in the prior art of radial MRI (for example "Magnetic Resonance Angiographie [sic]" by I. P. Arlart et al., ISBN 3-540-43975-7; or "Real-time MRI at a resolution of 20 ms" by Martin Uecker et al., NMR in Biomedicine Volume 23, Issue 8, pages 986-994, October 2010) and are therefore will not described in further detail here. In order to correct distortions in the EPI measurement (which can occur via B0 field changes or susceptibility changes due to the long readout time per excitation), two EPI measurements are in turn implemented with different start points. In the first EPI measurement (which is shown in FIG. 9), the raw data space is scanned and filled as previously described, beginning with the point 81, for example. In the second EPI measurement which is shown in FIG. 10, the scanning and the filling of the raw data space begins with the point 84, for example, thus shifted by an offset 87 relative to the first EPI measurement. On the basis of the second EPI measurement, a second complex magnetic resonance image is created and a distortion can be determined on the basis of the phase information from the first and second magnetic resonance image, and thus the magnetic resonance images can be corrected.

Figure 11:
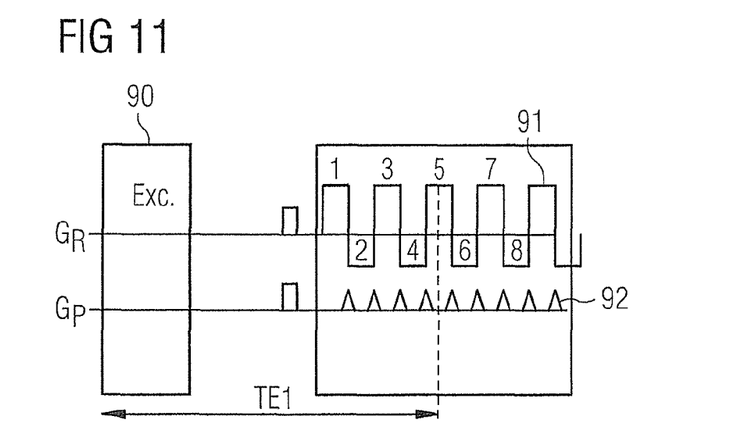
FIGS. 11 and 13 show sequence diagrams of an echoplanar imaging according to one embodiment of the present invention.
Figure 12:
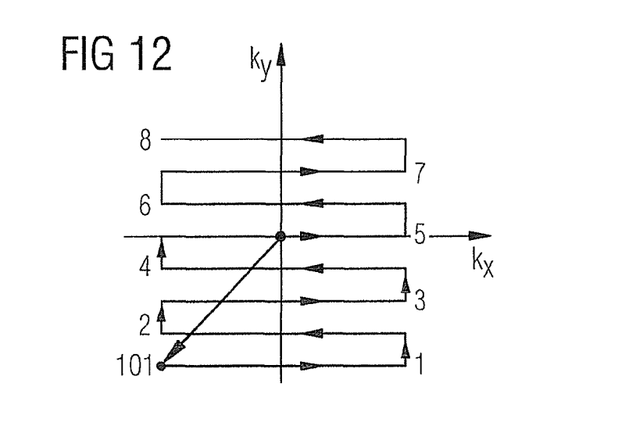
FIGS. 12 and 14 show raw data space scans given echoplanar imaging measurements according to FIG. 11 or, respectively, FIG. 13.
Figure 13:
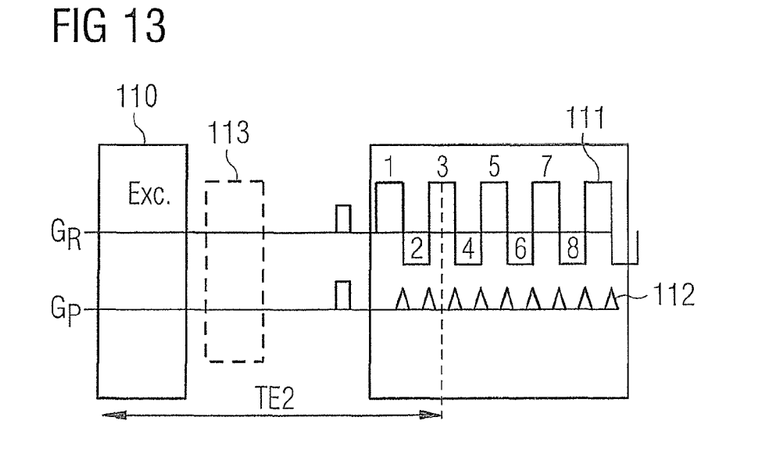
Figure 14:
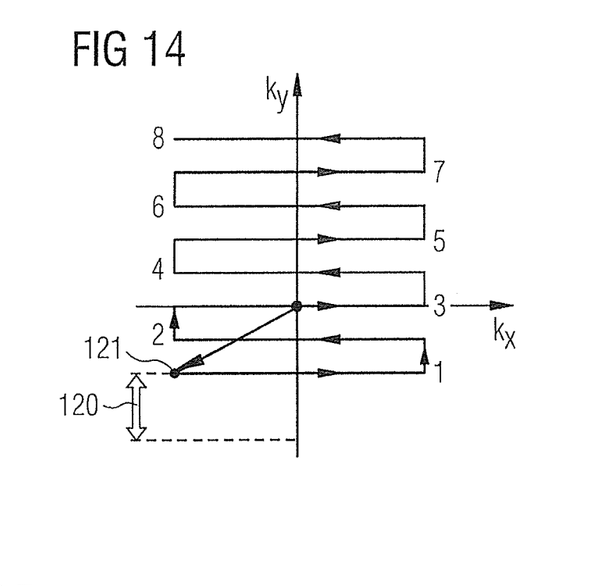

FIG. 11 through 14 show sequence diagrams and trajectories in raw data space for a distortion correction with the aid of the PLACE method. Only eight lines in raw data space are shown for reasons of clarity. In real EPI measurements, a significantly higher number of lines in the raw data space are typically scanned, for example 64 to 256 lines. FIG. 11 shows the sequence diagram for a first EPI measurement. After an excitation 90, the raw data space is read out line by line in a wandering manner from bottom to top, beginning at point 101 with the line 1 with the use of the readout gradient $G_R$ 91 and the phase coding gradient $G_p$ 92. The reference characters 1-8 thereby designate time ranges of FIG. 11 with corresponding lines of FIG. 12. After a time period TE1 the center of the raw data space is traversed, i.e. the middle of the fifth line. After the first EPI measurement according to FIGS. 11 and 12 has been implemented, the second EPI measurement according to FIGS. 13 and 14 is implemented. The workflow is essentially the same: after the excitation 110, the raw data space is scanned (beginning at a point 121 as shown in FIG. 14) with the use of the readout gradient $G_R$ 111 and the phase coding gradient $G_p$ 112, wherein the first line of FIG. 14 corresponds to the third line of FIG. 12, the second line of FIG. 14 corresponds to the fourth line of FIG. 12, the third line of FIG. 14 corresponds to the fifth line of FIG. 12 etc. The raw data space is thus scanned with an offset 120 of two lines. Without further measures, the fifth line (which, however, would correspond to the seventh line of FIG. 12) would thus be scanned in turn after the time period TE1. This would have the result that the sample values of corresponding points in raw data space would have different amplitudes due to this different scanning, and thus would produce different magnitudes in the corresponding magnetic resonance images. As is shown in FIG. 13, after the excitation 110 a delay 113 is therefore inserted such that the interval TE2 between the excitation 110 and the third line of the second EPI measurement is just as large as the time period TE1 between the excitation 90 and the fifth line in the first EPI measurement. No different amplitudes for corresponding sample points in raw data space thereby result due to the offset scanning of said raw data space. Therefore, the magnetic resonance images determined in such a manner can be used in functional magnetic resonance imaging, for example, in particular in time series of volume images in which small changes of the magnitudes are used in order to detect physiological BLOD (Blood Oxygenation Level Dependent Contrast) changes.

Figure 15:
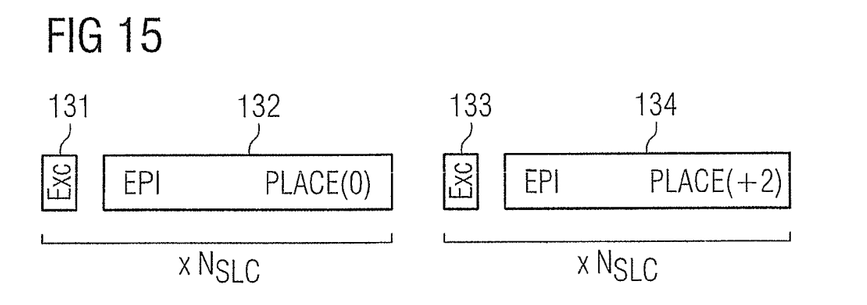
FIG. 15 schematically shows echoplanar imaging sequences in the case of a PLACE method according to the prior art.

FIG. 15 schematically shows how volume acquisitions are implemented in the prior art with the PLACE method with the aid of an echoplanar imaging and a distortion correction. An excitation 131 with a subsequent EPI measurement 132 is respectively implemented for a number $N_{SCL}$ of slices of the volume to be examined. For example, the EPI measurement 132 is implemented without offset (as shown in FIG. 12) and therefore as PLACE(0) (thus with offset of 0). After all slices $N_{SLC}$ have been acquired, the slices $N_{SLC}$ are rescanned in sequence, meaning that each slice is scanned with an EPI measurement 134 after an excitation 133. The EPI measurement 134 is implemented as shown in FIG. 14, for example, i.e. with an offset of two lines, for example, which is characterized by the designation PLACE(+2) in FIG. 15. $N_{SLC}$ first magnetic resonance images and $N_{SLC}$ second magnetic resonance images which respectively have phase information for image points of the corresponding magnetic resonance images are determined with the data of the $2N_{SLC}$ EPI measurements, and geometric distortions for the image points can be determined according to the PLACE method depending on the phase information. The time interval between corresponding images which are correlated in the PLACE method typically amounts to 2 to 3 seconds. A distortion correction can be negatively affected due to movements of the examination subject, for example breathing or heartbeat of a patient.

Figure 16:
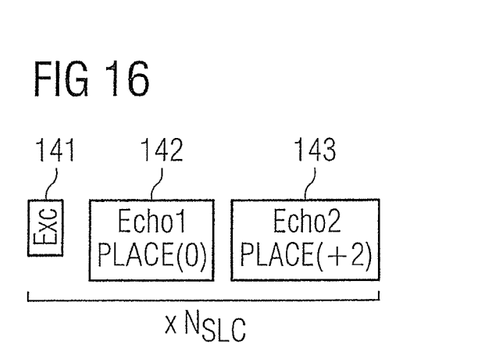
FIG. 16 schematically shows echoplanar imaging sequences for a PLACE method according to an embodiment of the present invention.

FIG. 16 shows a method optimized according to the present invention for the acquisition of an examination volume with the aid of echoplanar imaging. For the $N_{SLC}$ slices to be examined, the corresponding slice is respectively excited with a radio-frequency excitation 141 and is subsequently scanned with two EPI measurements, wherein the second measurement is scanned with an offset of two lines (for example) relative to the first measurement. The first EPI measurement 142 is thus scanned as shown in FIG. 12, for example, and the second measurement 143 is scanned as shown in FIG. 14. The time interval between the two scans now amounts to only a few milliseconds—50 ms, for example—so that the probability of patient movements is very small and the distortion correction can be implemented reliably with the PLACE method.

Figure 17:
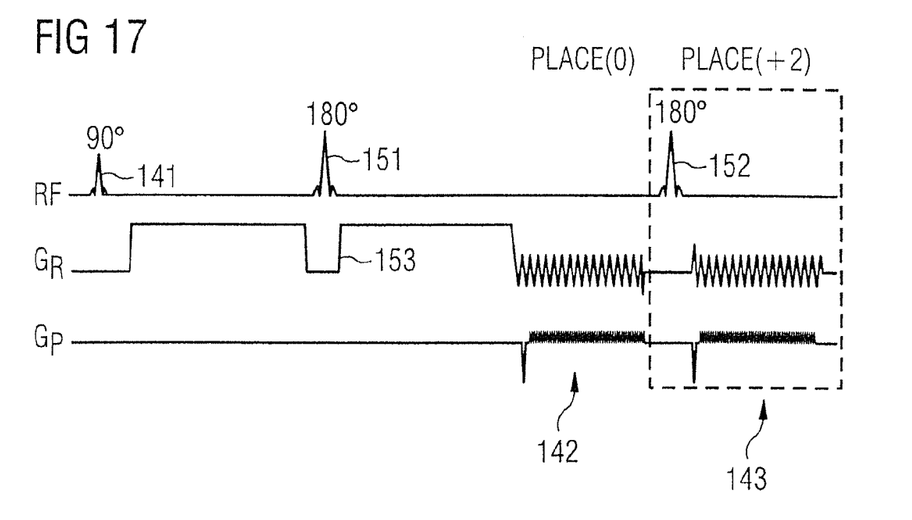
FIG. 17 shows details of an echoplanar imaging sequence of FIG. 16.

FIG. 17 shows a special embodiment for the method described in connection with FIG. 16. The two EPI measurements 142 and 143 are acquired as a multi-spin echo sequence. After the excitation 141, a first refocusing pulse 151 is applied and the first scan 142 of the raw data space is implemented. A second refocusing pulse 152 is subsequently applied and the offset scan 143 is implemented according to FIG. 14. Additionally, a diffusion preparation 153 (for example as shown in FIG. 17) can be applied in the readout direction or an arbitrarily different direction during the first refocusing pulse 151. The sequence shown in FIG. 17 is in particular advantageous when the time for the diffusion preparation primarily affects the sequence length (i.e. TR).

Figure 18:
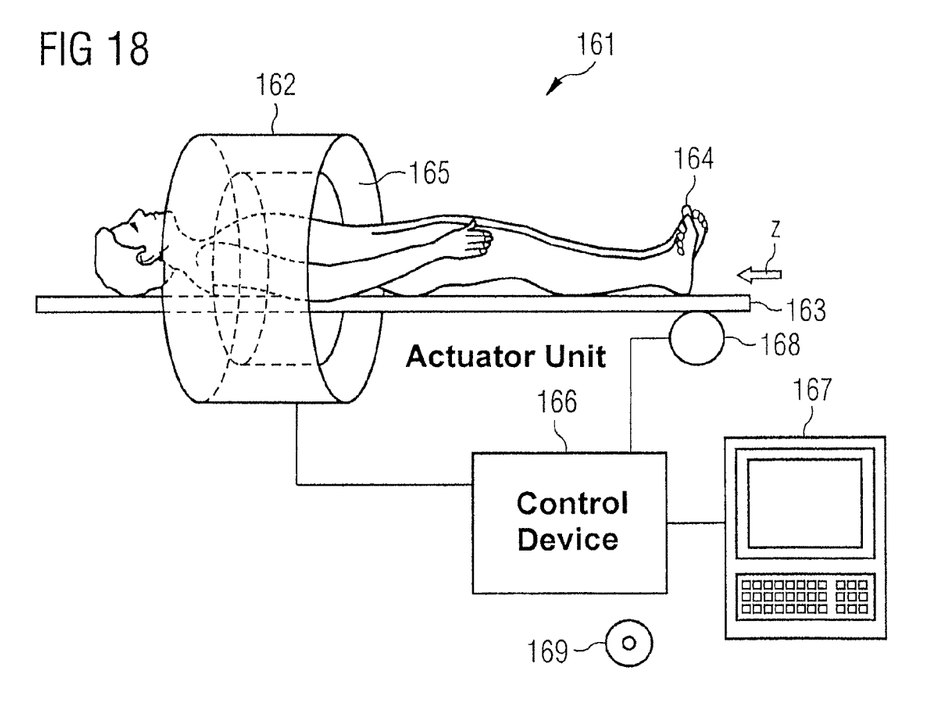
FIG. 18 schematically shows a magnetic resonance system according to an embodiment of the present invention.

FIG. 18 shows a schematic representation of a magnetic resonance system 161. The magnetic resonance system 161 unit the actual tomograph unit 162; an examination table 163 for a patient 164 which is located in an opening 165 of the tomograph unit 162; a control device 166; an evaluation device 167; and an actuator unit 168. The control device 166 controls the tomograph unit 162 and receives signals from the tomograph unit 162 which are acquired by said tomograph 162. The tomograph unit 162 has a basic field magnet (not shown) to generate a basic magnetic field B0, and the tomograph unit 162 has a gradient field system (not shown) to generate gradient magnetic fields. Furthermore, the tomograph unit 162 has one or more radio-frequency antennas to generate radio-frequency signals and receive measurement signals which are used by the control device 166 and the evaluation device 167 to generate magnetic resonance exposures. Furthermore, the control device 166 controls the actuator unit 168 in order to move the examination table 163 (together with the patient 164) along a direction Z through the opening 165 of the tomograph unit 162. For example, the control device 166 and the evaluation device 167 can be a computer with a monitor, a keyboard, a pointer input device (such as a mouse, for example) and a data medium 169 on which is stored electronically readable control information which is designed such that it can implement the previously described methods upon use of said data medium 169 in the evaluation device 167 and the control device 166.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for correcting distortion in spiral magnetic resonance imaging wherein raw magnetic resonance data are acquired with modulation of at least two gradients respectively in two spatial directions comprising:
   in a computer, automatically entering a first magnetic resonance raw data set, acquired after a single radio-frequency excitation, into k-space along a spiral trajectory in k-space, beginning at a first point of k-space;
   in said computer, automatically determining a first complex MR image from said first MR raw data set, said first complex MR image comprising first phase information for respective image points of said first MR image;
   in said computer, automatically entering a second MR raw data set, also acquired after a single radio-frequency excitation, into k-space along said spiral trajectory, beginning at a second point of k-space along said spiral trajectory that differs from said first point;
   in said computer, automatically determining a second complex MR image from said second MR raw data set, said second complex MR image comprising second phase information for respective image points of said second MR image;
   in said computer, automatically determining a geometric distortion for respective image points of said first MR image or said second MR image from said first and second phase information; and
   in said computer, automatically correcting said geometric distortion in said first MR image or in said second MR image, to produce at least one corrected MR image, and making said at least one corrected MR image available in electronic form at an output of said computer, as a data file.

2. The method as claimed in claim 1 comprising entering said first and second MR raw data sets into k-space along said spiral trajectory with a predetermined radius that decreases along said spiral trajectory.

3. The method as claimed in claim 1 comprising entering said first and second MR raw data sets into k-space along said spiral trajectory with a predetermined radius that increases along said spiral trajectory.

4. The method as claimed in claim 1 comprising entering said first and second MR raw data sets into k-space with a variable speed.

5. The method as claimed in claim 1 comprising entering said first and second MR raw data sets into k-space with a variable density.

6. The method as claimed in claim 1 comprising determining said geometric distortion by using a PLACE method to generate at least one of a field map and a displacement map.

7. A method for correcting distortion in radial magnetic resonance imaging wherein raw magnetic resonance data are acquired with modulation of at least two readout gradients respectively in two spatial directions comprising:
   in a computer, automatically entering a first magnetic resonance raw data set, acquired after a single radio-frequency excitation, into k-space along multiple radial trajectories in k-space respectively proceeding at different angles through a center of k-space, beginning at a first point of k-space;
   in said computer, automatically determining a first complex MR image from said first MR raw data set, said first complex MR image comprising first phase information for respective image points of said first MR image;
   in said computer, automatically entering a second MR raw data set, also acquired after a single radio-frequency excitation, into k-space along said radial trajectories, beginning at a second point of k-space along each radial trajectory that differs from said first point;
   in said computer, automatically determining a second complex MR image from said second MR raw data set, said second complex MR image comprising second phase information for respective image points of said second MR image;
   in said computer, automatically determining a geometric distortion for respective image points of said first MR image or said second MR image from said first and second phase information; and
   in said computer, automatically correcting said geometric distortion in said first MR image or in said second MR image, to produce at least one corrected MR image, and making said at least one corrected MR image available in electronic form at an output of said computer, as a data file.

8. The method as claimed in claim 7 comprising entering said first and second MR raw data sets into k-space with a variable speed.

9. The method as claimed in claim 7 comprising entering said first and second MR raw data sets into k-space with a variable density.

10. The method as claimed in claim 7 comprising determining said geometric distortion by using a PLACE method to generate at least one of a field map and a displacement map.

11. A method for correcting distortion in echo planar magnetic resonance imaging wherein raw magnetic resonance data are acquired modulation of a readout gradient and a phase-coding gradient respectively in different spatial directions, comprising:

operating a magnetic resonance data acquisition unit, while an examination subject is situated therein, to acquire a first magnetic resonance raw data set following a single radio-frequency excitation of nuclear spins in the subject, and to acquire a second magnetic resonance raw data set following a single excitation of nuclear spins in the subject;

operating the magnetic resonance data acquisition unit to delay a beginning of modulation of the readout gradient and the phase-coding gradient in the acquisition of said second magnetic resonance raw data set, after the single radio-frequency excitation after which said second magnetic resonance raw data set is acquired;

in a computer, automatically entering a first magnetic resonance raw data set in k-space along said predetermined trajectory into k-space, beginning at a first point of k-space;

in said computer, automatically determining a first complex MR image from said first MR raw data set, said first complex MR image comprising first phase information for respective image points of said first MR image;

in said computer, automatically determining entering a second MR raw data set into k-space along said predetermined trajectory, beginning at a second point of k-space along said predetermined trajectory that differs from said first point;

operating said magnetic resonance data acquisition unit with said delay to cause points of said predetermined trajectory to be scanned at same points in time relative to the respective radio-frequency excitation in the acquisition of said second magnetic resonance raw data set as corresponding points of said predetermined trajectory in the acquisition of the first magnetic resonance raw data set;

in said computer, automatically determining a second complex MR image from said second MR raw data set, said second complex MR image comprising second phase information for respective image points of said second MR image;

in said computer, automatically determining a geometric distortion for respective image points of said first MR image or said second MR image from said first and second phase information; and in said computer, automatically correcting said geometric distortion in said first MR image or in said second MR image, to produce at least one corrected MR image, and making said at least one corrected MR image available in electronic form at an output of said computer, as a data file.

12. The method as claimed in claim 11 comprising determining said geometric distortion by using a PLACE method to generate at least one of a field map and a displacement map.

13. A method for correcting distortion in echo planar magnetic resonance imaging comprising:

operating a magnetic resonance data acquisition unit to acquire first and second sets of raw magnetic resonance data with a single radio-frequency excitation of nuclear spins in a subject, with modulation of a readout gradient and a phase-coding gradient;

in a computer, automatically entering said first magnetic resonance raw data set into k-space along a predetermined trajectory in k-space, beginning at a first point of k-space;

in said computer, automatically determining a first complex MR image from said first MR raw data set, said first complex MR image comprising first phase information for respective image points of said first MR image;

in said computer, automatically entering said second MR raw data set into k-space along said predetermined trajectory, beginning at a second point of k-space along said predetermined trajectory that differs from said first point;

in said computer, automatically determining a second complex MR image from said second MR raw data set, said second complex MR image comprising second phase information for respective image points of said second MR image;

in said computer, automatically determining a geometric distortion for respective image points of said first MR image or said second MR image from said first and second phase information; and in said computer, automatically correcting said geometric distortion in said first MR image or in said second MR image, to produce at least one corrected MR image, and making said at least one corrected MR image available in electronic form at an output of said computer, as a data file.

14. The method as claimed in claim 13 comprising:

applying a first radio-frequency refocusing pulse to said subject before acquiring said first MR raw data set; and applying a second radio-frequency refocusing pulse to said subject between acquisition of said first MR raw data set and acquisition of said second MR raw data set.

15. The method as claimed in claim 14 comprising applying said first radio-frequency refocusing pulse with a magnetic preparation.

16. The method as claimed in claim 15 comprising applying a defusing-waiting gradient to said subject as said magnetic preparation.

17. The method as claimed in claim 13 comprising determining said geometric distortion by using a PLACE method to generate at least one of a field map and a displacement map.

18. A magnetic resonance apparatus comprising:

a magnetic resonance data acquisition unit configured to receive a subject therein;

a control unit configured to operate said magnetic resonance data acquisition unit to acquire a first set of magnetic resonance raw data following a single radio-frequency excitation of nuclear spins in the subject, and to acquire a second set of magnetic resonance raw data following a single radio-frequency excitation of nuclear spins in the subject, with modulation of at least two readout gradients respectively in two spatial directions;

a computer configured to automatically enter said first magnetic resonance raw data set into k-space along a spiral trajectory in k-space, beginning at a first point of k-space;

said computer being configured to automatically determine a first complex MR image from said first MR raw data set, said first complex MR image comprising first phase information for respective image points of said first MR image;

said computer being configured to automatically enter said second MR raw data set into k-space along said spiral trajectory, beginning at a second point of k-space along said spiral trajectory that differs from said first point;

said computer being configured to automatically determine a second complex MR image from said second MR raw data set, said second complex MR image comprising second phase information for respective image points of said second MR image;

said computer being configured to automatically determine a geometric distortion for respective image points of said first MR image or said second MR image from said first and second phase information; and said computer being configured to automatically correct said geometric distortion in said first MR image or in said second MR image, to produce at least one corrected MR image, and to make said at least one corrected MR image available in electronic form at an output of said computer, as a data file.

19. A magnetic resonance apparatus comprising:

a magnetic resonance data acquisition unit configured to receive a subject therein;

a control unit configured to operate said magnetic resonance data acquisition unit to acquire a first set of magnetic resonance raw data following a single radio-frequency excitation of nuclear spins in the subject, and to acquire a second set of magnetic resonance raw data with a single radio-frequency excitation of nuclear spins in the subject, with modulation of at least two readout gradients respectively in two spatial directions;

said computer being configured to automatically enter said first magnetic resonance raw data set into k-space along multiple radial trajectories in k-space respectively proceeding at different angles through a center of k-space, beginning at a first point of k-space of each radial trajectory;

said computer being configured to automatically determine a first complex MR image from said first MR raw data set, said first complex MR image comprising first phase information for respective image points of said first MR image;

said computer being configured to automatically enter said second MR raw data set into k-space along said radial trajectories, beginning at a second point of k-space along each radial trajectory that differs from said first point;

said computer being configured to automatically determine a second complex MR image from said second MR raw data set, said second complex MR image comprising second phase information for respective image points of said second MR image;

said computer being configured to automatically determine a geometric distortion for respective image points of said first MR image or said second MR image from said first and second phase information; and said computer being configured to automatically correct said geometric distortion in said first MR image or in said second MR image, to produce at least one corrected MR image, and to make said at least one corrected MR image available in electronic form at an output of said computer, as a data file.

20. A magnetic resonance apparatus comprising:

a magnetic resonance data acquisition unit configured to receive a subject therein;

a control unit configured to operate said magnetic resonance data acquisition unit to acquire first and second sets of magnetic resonance raw data in an echo planar imaging sequence, with a single radio-frequency excitation of nuclear spins in the subject and with modulation of a readout gradient and a phase-coding gradient;

a computer configured to automatically enter said first magnetic resonance raw data set in k-space along a predetermined trajectory into k-space, beginning at a first point of k-space;

said computer being configured to automatically determine a first complex MR image from said first MR raw data set, said first complex MR image comprising first phase information for respective image points of said first MR image;

said computer being configured to automatically enter said second MR raw data set into k-space along said predetermined trajectory, beginning at a second point of k-space along said predetermined trajectory that differs from said first point;

said computer being configured to automatically determine a second complex MR image from said second MR raw data set, said second complex MR image comprising second phase information for respective image points of said second MR image;

said computer being configured to automatically determine a geometric distortion for respective image points of said first MR image or said second MR image from said first and second phase information; and said computer being configured to automatically correct said geometric distortion in said first MR image or in said second MR image, to produce at least one corrected MR image, and to make said at least one corrected MR image available in electronic form at an output of said computer, as a data file.

21. A non-transitory, computer-readable data storage medium encoded with programming instructions that, when said storage medium is loaded into a computerized control and evaluation system of a magnetic resonance system that also includes a magnetic resonance data acquisition unit, cause said computerized control and evaluation system to:

receive a first set of magnetic resonance raw data acquired following a single radio-frequency excitation of nuclear spins in the subject, and a second magnetic resonance raw data set acquired with a single radio-frequency of nuclear spins in a subject, with modulation of at least two readout gradients respectively in two spatial directions;

automatically enter said first magnetic resonance raw data set into k-space along a spiral trajectory in k-space, beginning at a first point of k-space of said spiral trajectory;

automatically determine a first complex MR image from said first MR raw data set, said first complex MR image comprising first phase information for respective image points of said first MR image;

automatically enter said second MR raw data set into k-space along said spiral trajectory, beginning at a second point of k-space along said spiral trajectory that differs from said first point;

automatically determine a second complex MR image from said second MR raw data set, said second complex MR image comprising second phase information for respective image points of said second MR image;

automatically determine a geometric distortion for respective image points of said first MR image or said second MR image from said first and second phase information; and correct said geometric distortion in said first MR image or in said second MR image, to produce at least one corrected MR image, and make said at least one corrected MR image available in electronic form at an output of said computer, as a data file.

22. A non-transitory, computer-readable data storage medium encoded with programming instructions that, when said storage medium is loaded into a computerized control and evaluation system of a magnetic resonance system that also includes a magnetic resonance data acquisition unit, cause said computerized control and evaluation system to:

receive a first set of magnetic resonance raw data acquired following a single radio-frequency excitation of nuclear spins in the subject, and a second magnetic resonance raw data set acquired with a single radio-frequency of nuclear spins in a subject, with modulation of at least two readout gradients respectively in two spatial directions;

automatically enter said first magnetic resonance raw data set into k-space along multiple radial trajectory in k-space respectively proceeding at different angles through a center of k-space, beginning at a first point of k-space on each radial trajectory;

automatically determine a first complex MR image from said first MR raw data set, said first complex MR image comprising first phase information for respective image points of said first MR image;

automatically enter said second MR raw data set into k-space along said radial trajectories, beginning at a second point of k-space of each radial trajectory that differs from said first point;

automatically determine a second complex MR image from said second MR raw data set, said second complex MR image comprising second phase information for respective image points of said second MR image;

automatically determine a geometric distortion for respective image points of said first MR image or said second MR image from said first and second phase information; and correct said geometric distortion in said first MR image or in said second MR image, to produce at least one corrected MR image, and make said at least one corrected MR image available in electronic form at an output of said computer, as a data file.

23. A non-transitory, computer-readable data storage medium encoded with programming instructions that, when said storage medium is loaded into a computerized control and evaluation system of a magnetic resonance system that also includes a magnetic resonance data acquisition unit, cause said computerized control and evaluation system to:

receive first and second magnetic resonance raw data sets acquired in an echo planar imaging sequence with a single radio-frequency excitation of nuclear spins in a subject, and with modulation of a readout gradient and a phase coding gradient;

automatically enter said first magnetic resonance raw data set into k-space along a predetermined trajectory in k-space, beginning at a first point of k-space;

automatically determine a first complex MR image from said first MR raw data set, said first complex MR image comprising first phase information for respective image points of said first MR image of said predetermined trajectory;

automatically enter said second MR raw data set into k-space along said predetermined trajectory, beginning at a second point of k-space along said predetermined trajectory that differs from said first point;

automatically determine a second complex MR image from said second MR raw data set, said second complex MR image comprising second phase information for respective image points of said second MR image;

automatically determine a geometric distortion for respective image points of said first MR image or said second MR image from said first and second phase information; and correct said geometric distortion in said first MR image or in said second MR image, to produce at least one corrected MR image, and make said at least one corrected MR image available in electronic form at an output of said computer, as a data file.

24. A method as claimed in claim 1 comprising acquiring said second magnetic resonance raw data set following the same single radio-frequency excitation used to acquire said first magnetic resonance raw data set.

25. A method as claimed in claim 7 comprising acquiring said second magnetic resonance raw data set following the same single radio-frequency excitation used to acquire said first magnetic resonance raw data set.

26. A magnetic resonance apparatus as claimed in claim 18 wherein said control unit is configured to operate said magnetic resonance data acquisition unit to acquire said first and second sets of magnetic resonance raw data with the same single radio-frequency excitation of nuclear spins in the subject.

27. A magnetic resonance apparatus as claimed in claim 19 wherein said control unit is configured to operate said magnetic resonance data acquisition unit to acquire said first and second sets of magnetic resonance raw data with the same single radio-frequency excitation of nuclear spins in the subject.

* * * * *